United States Patent
Hsieh

(10) Patent No.: US 7,221,280 B2
(45) Date of Patent: May 22, 2007

(54) URINOUS WET ALARM

(75) Inventor: Shih-Nan Hsieh, Taipei (TW)

(73) Assignee: Lightak Electronics Corp., Taipei (TW)

( * ) Notice: Subject to any disclaimer, the term of this patent is extended or adjusted under 35 U.S.C. 154(b) by 26 days.

(21) Appl. No.: 10/862,429

(22) Filed: Jun. 8, 2004

(65) Prior Publication Data

US 2005/0270162 A1  Dec. 8, 2005

(51) Int. Cl.
*G08B 21/00* (2006.01)
(52) U.S. Cl. ............... 340/604; 340/605; 340/608; 73/304 R
(58) Field of Classification Search ......... 340/604, 340/605, 608, 620; 73/304 R
See application file for complete search history.

(56) References Cited

U.S. PATENT DOCUMENTS

2003/0020615 A1* 1/2003 Zand et al. .............. 340/573.5

2004/0030309 A1* 2/2004 Huang ...................... 604/361

FOREIGN PATENT DOCUMENTS

JP 11000350 A * 1/1999
TW 210012 7/1993

* cited by examiner

*Primary Examiner*—Jeffery Hofsass
*Assistant Examiner*—Hongmin Fan
(74) *Attorney, Agent, or Firm*—Birch, Stewart, Kolasch & Birch, LLP

(57) ABSTRACT

A urinous wet alarm to detect a soaked diaper and generate an audio alarm to alert replacement includes a shell to house a test IC. The test IC connects to a lithium battery, a thin alarm speaker and one end of a sensing unit which is a pliable, elongate, narrow and thin plate and has a detection circuit consisting of two conductive wires of opposite polarity extended from the shell. The sensing unit may be inserted into a test insertion hole formed on a diaper during production. Urine soaked the fluid absorption layer of the diaper makes the conductive wires conductive, and the test IC determines the urine overflow condition to activate the thin alarm speaker to generate an audio alarm.

6 Claims, 4 Drawing Sheets

URINOUS WET ALARM

FIELD OF THE INVENTION

The present invention relates to a urinous wet alarm and particularly to an alarm to detect wet diaper caused by urination and generate audio alarm.

BACKGROUND OF THE INVENTION

There are many types of diapers on the market that offer wide selections of functions. And many patents have been disclosed in this field. Most of them focus on the improvement of fluid absorption layers, inner protection layer material or elastic band of the diaper.

The widely used diapers are the common paper diapers that merely protect users from incontinence or urine overflow (namely the urination exceeds the fluid absorption saturation limit of the diaper) and prevent clothes and bed sheets from being smeared. When urine overflow occurs to an infant wrapped by the diaper and the parents do not replace the smeared diaper timely due to negligence, infant's hip could be infected with bacteria. For adult users who suffer from incontinence or loss of sense (such as after surgery and patient's sense not yet recovers), wearing such type of diaper is not comfortable. While some improvements have been made on the inner fluid absorption layer and elastic band, urine overflow could still happen and replacement is not being made timely.

To overcome the problem mentioned above, some vendors adopt modern electronic technologies and use electronic audio effect and electronic conductive circuits on the diaper. Whenever the diaper is soaked with excretion, the circuits become conductive and an electronic audio alarm is generated to alert nurses to replace the diaper. For instance, R.O.C. patent No. 210012 entitled "Improved diaper with a separated audio alarm" discloses such a technique that has a conductive circuit consisting of two parallel metal wires to detect urinous wet. But it cannot detect a larger area. In the event that urine seeps through between the two parallel metal wires or overflows and seeps through outside the two metal wires, it is not effective. Moreover, to lay conductive wires in the diaper increases fabrication cost and the price. As the diaper is a household goods that is consumed at huge quantity, to set the price too high will discourage consumers from buying.

SUMMARY OF THE INVENTION

The primary object of the present invention is to provide a urinous wet alarm to detect a wet diaper and generate an audio alarm.

The detection is accomplished through a shell and a pliable, elongate, narrow and thin sensing unit extended from the shell. It has a detection circuit consisting of two conductive wires of opposite polarity. The sensing unit has one end connecting to a test IC and the detection circuit. The test IC is coupled with a lithium battery and a thin alarm speaker. The sensing unit may be inserted into a test insertion hole formed on the diaper during production to perform detection. When the fluid absorption layer is soaked with urine and saturated, the detection circuit becomes conductive and the thin alarm speaker is activated to generate an audio alarm.

Another object of the invention is to provide a urinous wet alarm that is not discarded with the used diaper. It may be wiped and cleaned to couple with a new diaper to be used repeatedly. It does not change the structure of the diaper and does not increase the cost thereof. It is affordable to the general households and can enhance economic effectiveness.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENT

Figure 1:
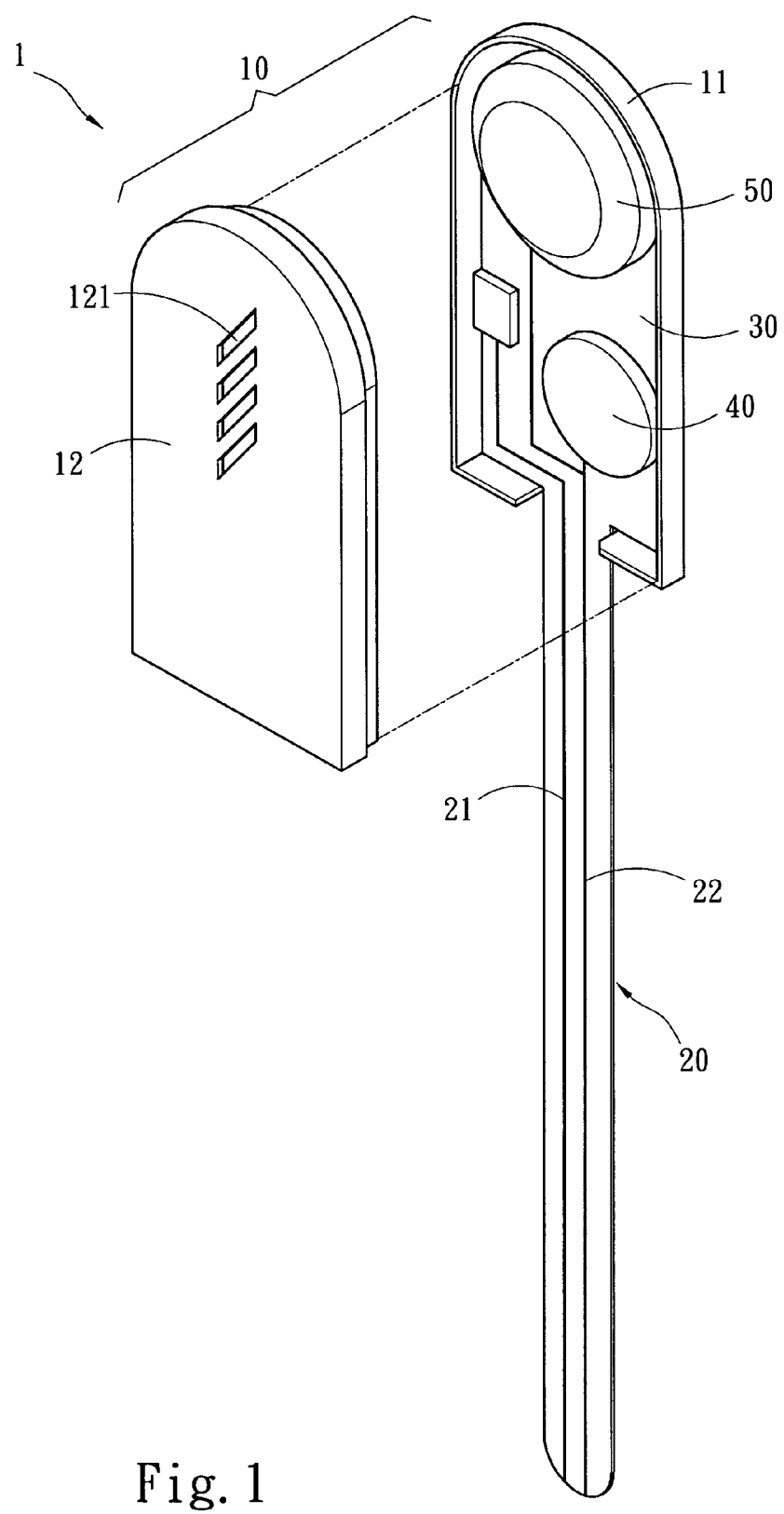
FIG. 1 is an exploded view of the urinous wet alarm of invention.
Figure 2:
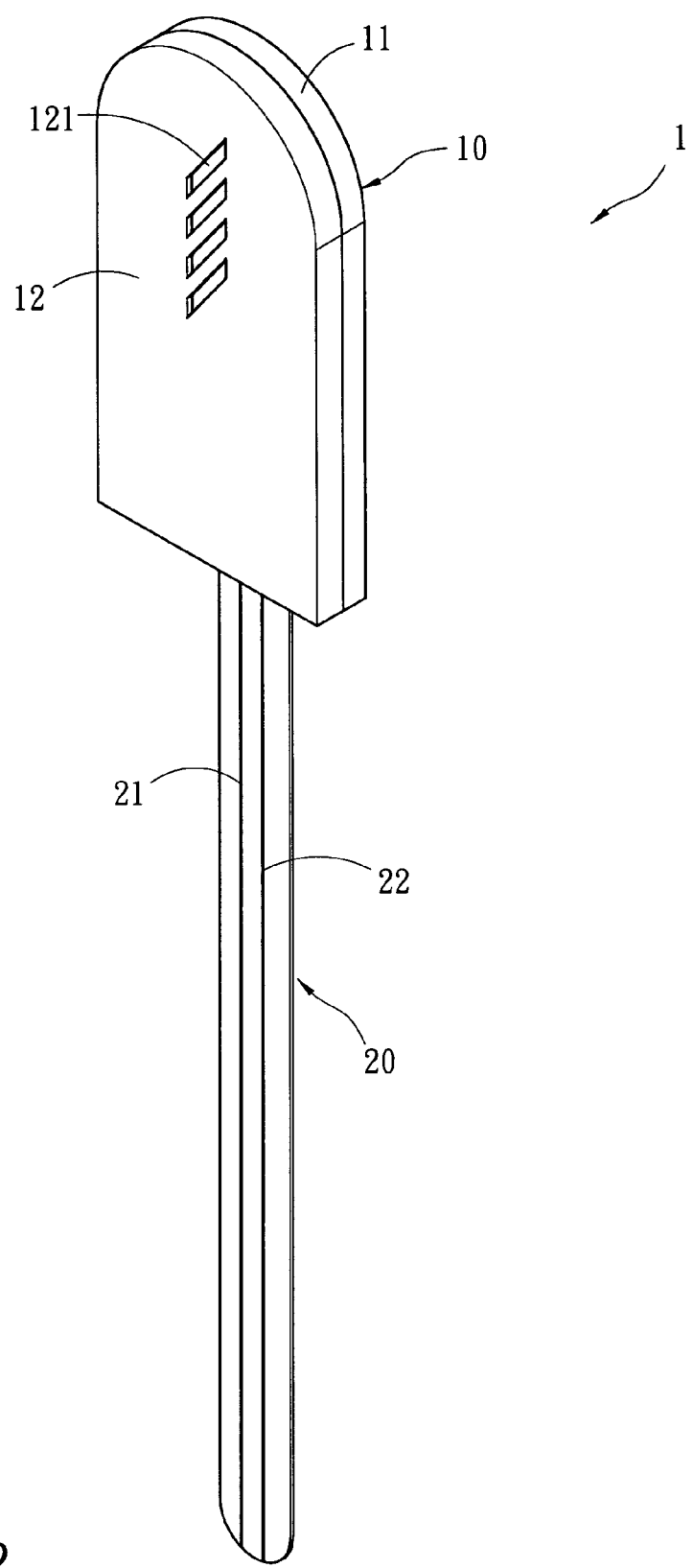
FIG. 2 is a perspective view of the urinous wet alarm of the invention.
Figure 3:
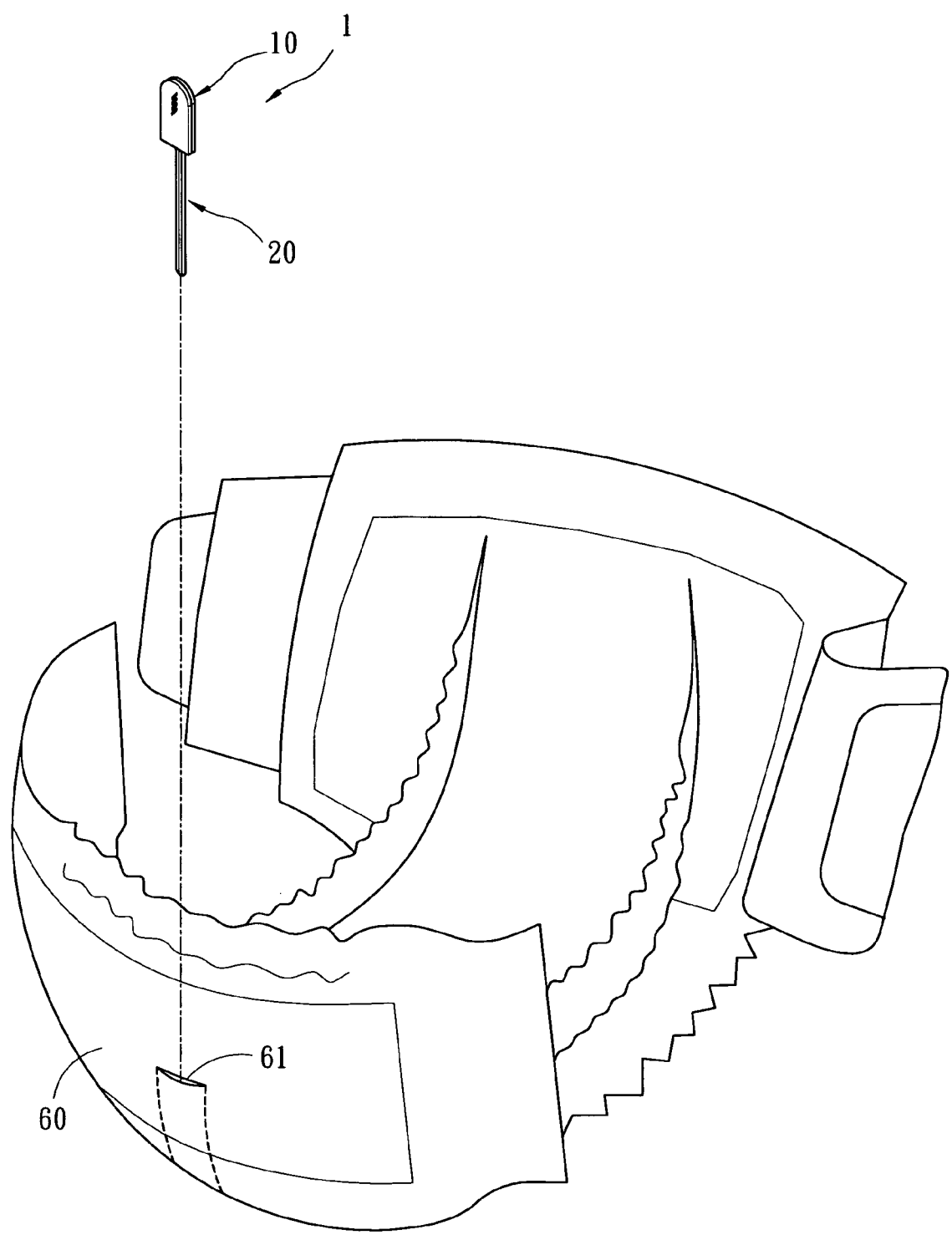
FIG. 3 is a schematic view of the urinous wet alarm of the invention before coupling with a diaper.

Please referring to FIGS. 1, 2 and 3, the urinous wet alarm 1 according to the present invention aims to generate a signal or alert for replacement according to the soaked condition of a diaper 60. The diaper 60 has a test insertion hole 61 formed thereon corresponding to the lower abdomen portion during production. The invention includes:

a shell 10 consisting of a plate 11 and a cap 12 to encase electronic elements of the alarm of the invention. The cap 12 has audio slots 121 formed on the surface;

a sensing unit 20 formed in a pliable, elongate, narrow and thin plate having one end attached to the plate 11. It has a detection circuit which consists of two conductive wires 21 and 22 of opposite polarity to detect urine soaking condition. In order to prevent the conductive wires 21 and 22 from generating signals from detecting a small amount of urine and result in replacing the diaper 60 too frequently, the detection side of the conductive wires 21 and 22 is on the back side of the fluid absorption layer and is attached to the outer fabric layer to detect the urine overflowed and seeped through the inner layers of the diaper 60. When the urine seeps through the fluid absorption layer and soaks the surface of the conductive wires 21 and 22 through capillary action, due to the interval of the conductive wires 21 and 22 is very small, the urine will attach to the conductive wires 21 and 22 of two opposite polarity and make them conductive to generate and output a detection signal; and a test IC 30 located above the sensing unit 20 and connected to the conductive wires 21 and 22 to receive the output detection signal when they become conductive. The test IC 30 links to a lithium battery 40 and a thin alarm speaker 50.

The test IC 30, lithium battery 40 and thin alarm speaker 50 are located in the shell 10 encased by the plate 11 and the cap 12. It may be used on the diaper 60 that has the test insertion hole 61 formed thereon during production to become part of the urinous wet alarm 1 of the invention.

Figure 4:
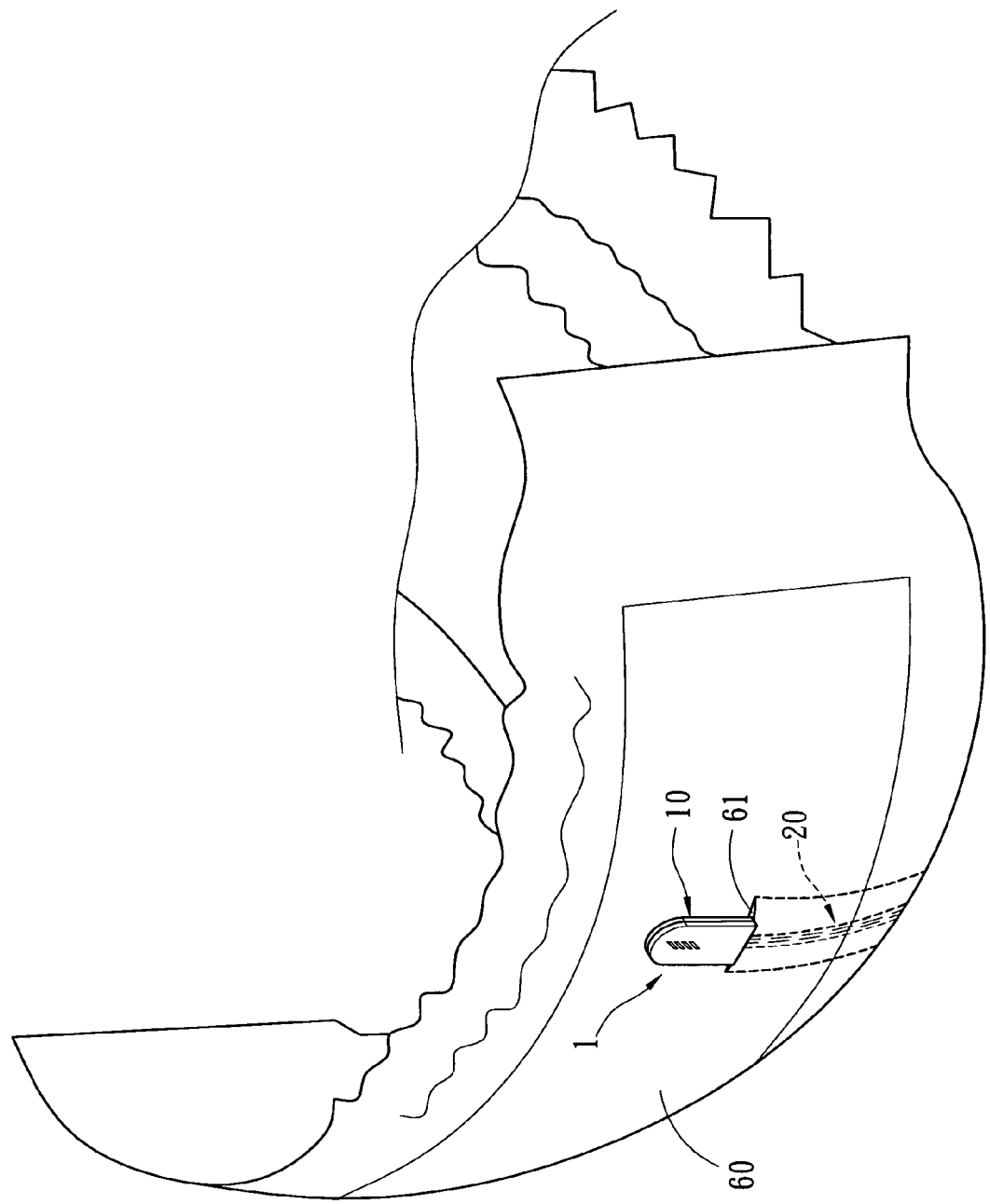
FIG. 4 is a schematic view of the urinous wet alarm of the invention coupled with a diaper when in use.

Refer to FIGS. 3 and 4 for the invention in a use condition. The diaper 60 has the test insertion hole 61 formed on the inner side of the fluid protection layer corresponding to the lower abdomen portion during production to receive the sensing unit 20 of the urinous wet alarm 1 to detect the urine overflowing and seeping through the inner layers of the diaper 60. When the urine seeps through the absorption layer due to capillary action to the surface to the conductive wires 21 and 22 that have a small interval, the urine attaches to the conductive wires 21 and 22 of two opposite polarity and makes them conductive. The sensing unit 20 determines the urine overflow condition and outputs a detection signal which is transmitted to the test IC 30, and an audio alarm is generated through the thin alarm speaker 50 to alert the soaked condition of the diaper 60. The urinous wet alarm 1 may be used repeatedly. It may be removed from the used and soaked diaper 60, and be wiped and cleaned, and to be reused on a new diaper 60 by inserting into the test insertion hole 61. As it is not thrown away with the used diaper 60, and may be reused repeatedly, it does not increase the cost very much. It is economic and useful, and affordable to the general households that have to use it.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A urinous wet alarm for detecting urine overflow on a diaper exceeding a fluid absorption saturation limit and generating an audio alarm, comprising:

a shell;

a reusable sensing unit having one end located in the shell and a detection circuit;

a test IC connecting to the detection circuit; and a lithium battery and a thin alarm speaker connecting to the test IC;

the sensing unit having a reusable distal end outside the shell to be inserted between an inner side of a fluid protection layer of a diaper and inner layers of the diaper to perform detection, the distal end of the sensing unit carrying conductive wires on the side toward the fluid protection layer, the detection circuit becoming conductive by urine seeping through inner layers of the diaper to generate an audio alarm through the thin alarm speaker.

2. The urinous wet alarm of claim 1, wherein the diaper has a test insertion hole to receive the reusable distal end of the sensing unit to perform detection.

3. The urinous wet alarm of claim 2, wherein the test insertion hole of the diaper is formed during production.

4. The urinous wet alarm of claim 1, wherein the shell includes a plate and a cap.

5. The urinous wet alarm of claim 1, wherein the cap has audio slots.

6. The urinous wet alarm of claim 1, wherein the sensing unit is a pliable, elongate, narrow and thin plate.

* * * * *